United States Patent

Hines et al.

(10) Patent No.: US 9,146,193 B2
(45) Date of Patent: Sep. 29, 2015

(54) SCATTEROMETRY METROLOGY METHODS AND METHODS OF MODELING FORMATION OF A VERTICAL REGION OF A MULTILAYER SEMICONDUCTOR SUBSTRATE TO COMPRISE A SCATTEROMETRY TARGET

(71) Applicant: Micron Technology, Inc., Boise, ID (US)

(72) Inventors: Danielle Hines, Boise, ID (US); Daniel E. Engelhard, Boise, ID (US); Fan Ming, Boise, ID (US)

(73) Assignee: Micron Technology, Inc., Boise, ID (US)

(*) Notice: Subject to any disclaimer, the term of this patent is extended or adjusted under 35 U.S.C. 154(b) by 106 days.

(21) Appl. No.: 14/147,417

(22) Filed: Jan. 3, 2014

(65) Prior Publication Data

US 2015/0192514 A1 Jul. 9, 2015

(51) Int. Cl.
*G06F 17/50* (2006.01)
*G01N 21/47* (2006.01)
*G01N 21/21* (2006.01)
*G01B 11/02* (2006.01)

(52) U.S. Cl.
CPC ............ *G01N 21/4738* (2013.01); *G01B 11/02* (2013.01); *G01N 21/21* (2013.01); *G06F 17/5009* (2013.01); *G06F 17/5072* (2013.01); *G01N 2201/061* (2013.01)

(58) Field of Classification Search
None
See application file for complete search history.

(56) References Cited

U.S. PATENT DOCUMENTS

| 7,123,366 | B2 | 10/2006 | Scheiner et al. |
| 7,187,456 | B2 | 3/2007 | Scheiner et al. |
| 7,292,335 | B2 | 11/2007 | Brill et al. |
| 7,327,476 | B2 | 2/2008 | Cohen et al. |
| 7,427,774 | B1 | 9/2008 | Mantz et al. |
| 7,495,782 | B2 | 2/2009 | Finarov et al. |
| 7,642,550 | B2 | 1/2010 | Taylor |
| 7,663,768 | B2 | 2/2010 | Finarov et al. |

(Continued)

OTHER PUBLICATIONS

Muthinti et al., "Characterization of e-beam patterned grating structures using Mueller matrix based scatterometry," J. Micro-Nanolith. MEMS MOEMS vol. 12(1), 013018, Jan.-Mar. 2013, 11 pages.*

(Continued)

*Primary Examiner* — Leigh Garbowski
(74) *Attorney, Agent, or Firm* — Wells St. John, P.S.

(57) ABSTRACT

A scatterometry target formed relative to an elevationally outermost surface of a substrate includes features having an optical property that is different from that of spaces between the features. The substrate has spaced-apart parallel elongated blocking lines having an optical property different from that of spaces between the blocking lines. The blocking lines are elevationally inward of the target features. The target features and the blocking lines overlap within a same vertical region of the substrate. Polarized electromagnetic radiation having multiple wavelengths is impinged onto the scatterometry target. Pitch of the blocking lines is less than the smallest wavelength of the impinged radiation. The blocking lines reduce spectrum variation to below a detectable level for any polarized electromagnetic radiation passing to elevationally inward of the blocking lines. Electromagnetic radiation that is reflected from the scatterometry target from the impinging is detected, and therefrom a property associated with the target features and/or spaces between the target features is determined.

35 Claims, 4 Drawing Sheets

(56) References Cited

U.S. PATENT DOCUMENTS

| | | |
|---|---|---|
| 7,747,424 B2 | 6/2010 | Opsal et al. |
| 7,808,638 B2 | 10/2010 | Bevis |
| 7,864,343 B2 | 1/2011 | Finarov et al. |
| 7,883,907 B2 | 2/2011 | Taylor |
| 8,023,122 B2 | 9/2011 | Finarov et al. |
| 8,142,965 B2 | 3/2012 | Yoel |
| 8,183,701 B2 | 5/2012 | Shih et al. |
| 8,289,515 B2 | 10/2012 | Cohen et al. |
| 8,531,678 B2 | 9/2013 | Finarov et al. |

OTHER PUBLICATIONS

Allgair et al.; A Review of Scatterometry for Three-Dimensional Semiconductor Feature Analysis; Furture Fab International, Issue 19; Jun. 28, 2005; 4 pp.

Jiang et al.; Characterization of the Poly Gate ACI Structure with Laser Based Angle Resolved Multiple Wavelength Scatterometry, Rudolph Technologies; SPIE; Feb. 2008; pp. 1-4.

Juan, H.; Real-Time Scatterometry for Critical Dimensions Measurements in Lithography; National University of Singapore; 2008; 5 pp.

McNeil et al.; Scatterometry Applied to Microelectronics Processing; IEEE; Jul. 24-28, 2004; pp. 37-38.

Physical Modeling Using NovaMARS; NOVA; http://www.novameasuring.com/; 2012; pp. 1-5.

Thony et al.; Review of CD Measurement and Scatterometry; American Institute of Physics; 2003; pp. 381-388.

Vaid et al.; Holistic metrology approach; hybrid metrology utilizing scatterometry, critical dimension-atomic force microscope and critical dimension-scanning electron microscope; Micro/Nanotlithography. MEMS, and MOEMS, vol. 10; Oct.-Dec. 2011; pp. 043016-1-043016-13.

Vaid et al.; Simultaneous Measurement of Optical Properties and Geometry of Resist Using Multiple Scatterometry Gratings; Proc. of SPIE, vol. 7638; 2010; pp. 76381H-1-76381H-12.

Wurm et al.; Evaluation of Scatterometry Tools for Critical Dimension Metrology; DGaO Proceedings 2005; 2 pp.

\* cited by examiner

SCATTEROMETRY METROLOGY METHODS AND METHODS OF MODELING FORMATION OF A VERTICAL REGION OF A MULTILAYER SEMICONDUCTOR SUBSTRATE TO COMPRISE A SCATTEROMETRY TARGET

TECHNICAL FIELD

Embodiments disclosed herein pertain to scatterometry metrology methods and to methods of modeling formation of a vertical region of a multilayer semiconductor substrate to comprise a scatterometry target.

BACKGROUND

Lithography is used in various applications for producing patterned structures, for example in the manufacture of integrated circuits, flat panel displays, micro-electro-mechanical systems, micro-optical systems, etc. During manufacture, a substrate typically undergoes a sequence of lithography-etching steps to produce the various features to result in a desired pattern within the uppermost portion of the substrate. The resultant pattern may be analyzed in a non-destructive manner using metrology techniques to determine, for example, placement and/or dimensions of the features or spaces between the features in the pattern, or to determine thickness or other attribute of deposited material.

One example metrology technique is scatterometry which impinges electromagnetic radiation onto a substrate pattern and analyzes spectral characteristics of reflected radiation to determine certain parameters of the pattern. This is done by comparing spectrographic characteristics of the reflected radiation to a theoretical or simulated ideal expectation representing what would have been achieved had perfect deposition, processing, patterning, and spectral analysis occurred. A software modeling process may be used to arrive at the desired theoretical ideal spectral characteristics. To be accurate, the model used during the modeling process must take into consideration the structure and composition of the pattern under analysis as well as structure and composition of material that is elevationally inward of the outermost pattern being analyzed. This is because some of the incident radiation will pass through the pattern into substrate material therebelow. It then passes through such material, reflects off of a base substrate, and passes back through the material to be detected and analyzed as part of the reflected radiation from the outermost pattern. Such adds significant complexity and opportunity for error associated with the software modeling, particularly with anticipated circuitry designs that may include tens or a hundred or more layers of various materials and structures beneath the outermost pattern being analyzed.

Additionally, scatterometry analysis typically occurs with respect to a patterned test or target area that is laterally displaced from the substrate area within which actual operative components are being fabricated. For example, integrated circuitry fabrication commonly forms the same circuitry within multiple spaced die areas on a larger substrate also known as a semiconductor wafer. These die areas are separated by what is commonly referred to as kerf, street, or scribe-line area that is ultimately cut-through to separate the finished die areas into singulated die or chips. The scatterometry targets are typically formed within this street area at different x-y locations for the different levels of patterning and correspond with the patterning that occurs at that level with respect to the circuitry being formed in the die areas. The street area within which the scatterometry targets are formed are among the largest open areas on the wafer. This can lead to dishing in the street area during polishing of the wafer. Dishing can result in height differences between the outermost surface of the scatterometry target and the surface of the corresponding pattern in the die areas. This can result in fundamental patterning problems and other processing issues that may make it difficult or impossible to create a scatterometry target which closely mimics the patterning in the die area.

While aspects of the invention were motivated in addressing some of the above issues, the inventions disclosed herein are in no way so-limited unless referred to in a specific claim under analysis.

DETAILED DESCRIPTION OF EXAMPLE EMBODIMENTS

Embodiments of the invention encompass scatterometry metrology methods and methods of modeling formation of a vertical region of a multilayer semiconductor substrate to comprise a scatterometry target. In this document, vertical is a direction generally orthogonal to horizontal, with horizontal referring to a general direction along a primary surface relative to which a substrate is processed during fabrication. Further, "vertical" and "horizontal" as used herein are generally perpendicular directions relative one another independent of orientation of the substrate in three-dimensional space. Additionally, "elevational" and "elevationally" are with reference to the vertical direction.

Figure 1:
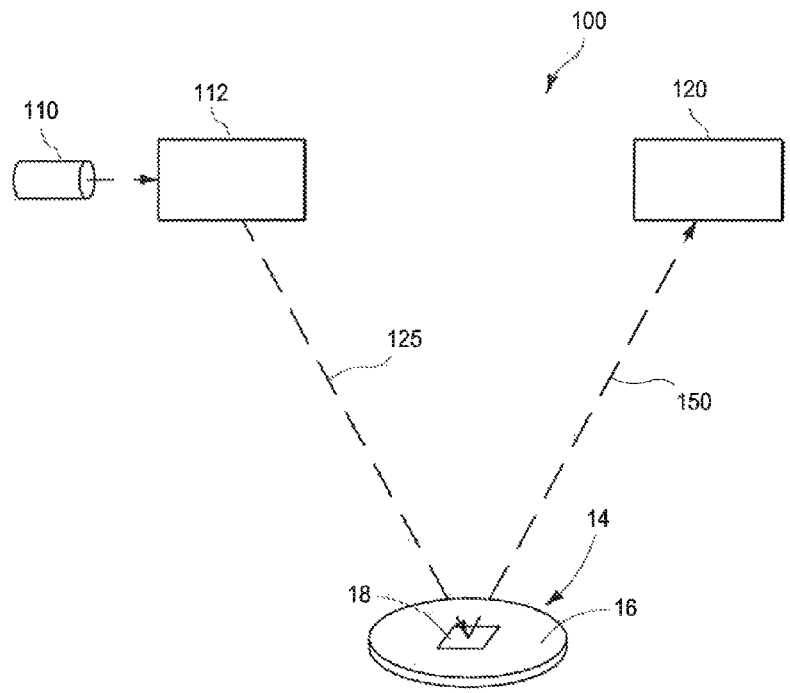
FIG. 1 is a diagrammatic schematic of a metrology tool or system usable in accordance with embodiments of the invention.

FIG. 1 diagrammatically illustrates an example scatterometry-based tool or system 100 usable in carrying out methods of the invention. System 100 includes an electromagnetic radiation source 110 capable of emitting a spectrum (i.e., multiple different wavelengths) of electromagnetic radiation. Examples include radiation within the visual, infrared, violet, and/or ultra-violet spectrums. A device 112 may process and/or otherwise direct the electromagnetic radiation emanating from source 110 to impinge upon a substrate 14 having an elevationally outermost surface 16. Incident radiation 125 from device 112 is impinged upon a scatterometry target 18 that has been formed relative to surface 16. Target 18 may be covered with a protective material through which the incident radiation is transmissive. Accordingly in this document, the scatterometry target is not necessarily part of the elevationally outermost surface at least at the time of impinging radiation thereon. Regardless, reflected radiation 150 arrives at a detector 120 for analysis to determine some attribute with respect to material and/or structure within scatterometry target 18. Scatterometry target 18 in FIG. 1 is shown in greatly exaggerated size, and multiple of the same or different construction targets 18 may be provided with respect to elevationally outermost surface 16 of substrate 14. Substrate 14 and incident radiation 125 may be moved relative one another for analyzing different scatterometry targets 18 at different x-y locations on substrate 14.

By way of examples only, example such equipment is described in U.S. Pat. Nos. 7,123,366, 7,292,335, 7,327,476, 7,427,774, 7,495,782, 7,663,768, 7,747,424, 7,808,638, 7,864,343, 7,883,907, 8,023,122, 8,142,965, 8,183,701, 8,289,515, and 8,531,678. Additionally, scatterometry tools usable in accordance with the invention are commercially available from companies such as KLA-Tencor Corporation, Rudolph Technologies, Inc., Nova Measuring Instruments Ltd., and Nanometrics Incorporated. Commercially available modeling software (e.g., NovaMARS® available from Nova Measuring Instruments Ltd.) is associated with such equipment and is usable to derive theoretical or simulated spectra of reflected radiation for comparison with the actual reflected spectra for determining an attribute of material and/or structure within the target areas relative to theoretical ideal processing. Additional existing or yet-to-be-developed equipment or software may be used.

Figure 2:
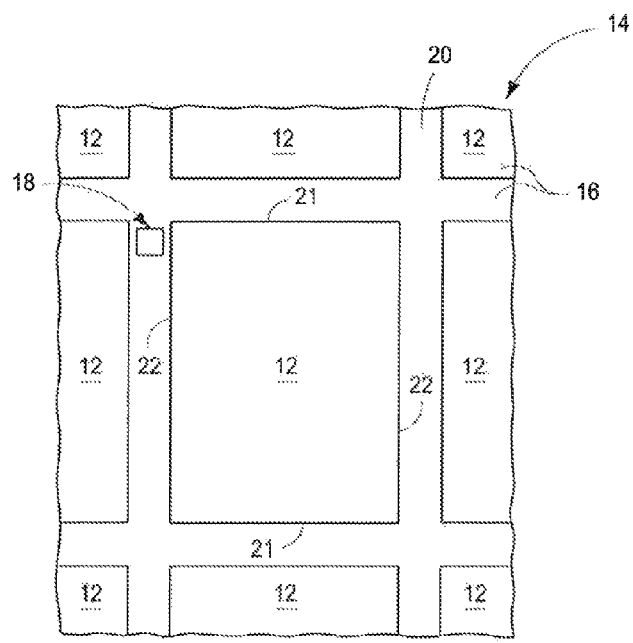
FIG. 2 is an enlarged diagrammatic top view of a small part of a substrate shown in use with the tool or system in FIG. 1.

Referring to FIG. 2, a very small portion of substrate 14 is shown having scatterometry target 18 that has been formed relative to elevationally outermost substrate surface 16. Substrate 14 may comprise a semiconductor substrate. In the context of this document, the term "semiconductor substrate" or "semiconductive substrate" is defined to mean any construction comprising semiconductive material, including, but not limited to, bulk semiconductive materials such as a semiconductive wafer (either alone or in assemblies comprising other materials thereon), and semiconductive material layers (either alone or in assemblies comprising other materials). The term "substrate" refers to any supporting structure, including, but not limited to, the semiconductive substrates described above. Substrate 14 may comprise integrated circuitry or other components in fabrication, and in one embodiment may include rectangular die areas 12 having street area 20 there-between, with target 18 having been formed within street area 20. Rectangular die areas 12 may be considered as comprising one pair of opposing sides or edges 21 and another pair of opposing sides or edges 22.

Figure 4:
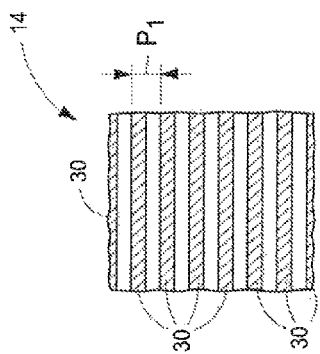
FIG. 4 is a sectional view taken through line 4-4 in FIG. 3.
Figure 5:
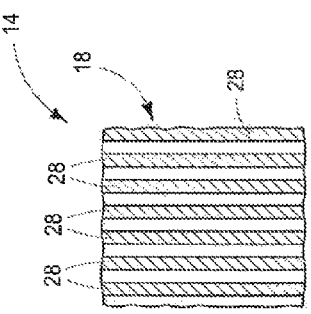
FIG. 5 is a sectional view taken through line 5-5 in FIG. 3.
Figure 3:
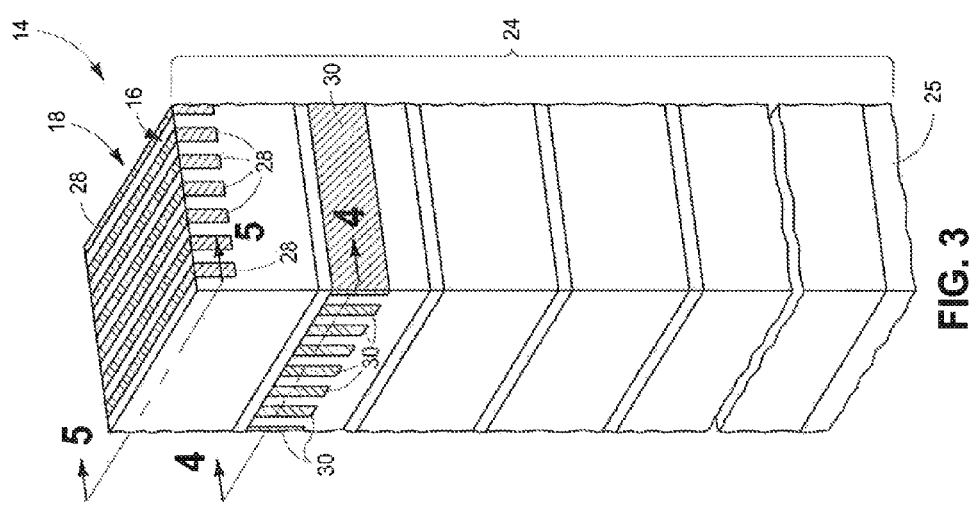
FIG. 3 shows an even smaller part of the FIG. 2 substrate and is a diagrammatic fragmented view of a vertical portion or region thereof.

FIG. 3 is a fragmentary perspective view of a vertical region 24 of substrate 14 showing a very small portion of example scatterometry target 18, with FIGS. 4 and 5 being different sectional views of vertical region 24. Example substrate 14 is shown as comprising some base substrate 25 (e.g., monocrystalline silicon) having numerous materials formed thereover. Scatterometry target 18 comprises features 28 having an optical property (i.e., an effect on impinging light or other electromagnetic radiation) that is different from that of spaces between such features.

Substrate 14 has been formed to comprise spaced-apart parallel elongated blocking lines 30 that are elevationally inward of target features 28, with target features 28 and blocking lines 30 overlapping (i.e., at least partially in or relative to x-y space) within the same vertical region 24 of substrate 14. In one embodiment the blocking lines comprise metal. In the context of this document, "metal" includes any elemental metal, an alloy of elemental metals, and conductive metal compounds. Blocking lines 30 have an optical property different from that of spaces between the blocking lines. For example, blocking lines 30 may be compositionally and/or structurally blocking or opaque to certain incident radiation whereas material between blocking lines 30 may be substantially transparent enabling such radiation to pass therethrough. Blocking lines 30 are formed to have a pitch which is less than the smallest wavelength of polarized electromagnetic radiation having multiple wavelengths that is to be impinged onto scatterometry target 18. In one embodiment and as shown, blocking lines 30 are elevationally spaced from target features 28.

Blocking lines 30 may individually be of uniform or variable width, be linearly straight, curvilinear, a combination of different angled straight and/or curved segments, etc., as may be the material of the spaces between blocking lines 30. Further, all blocking lines 30 may be of the same or different shape and configuration within a given scatterometry target 18, and may be of constant or varying pitch within scatterometry target 18. By way of example only, blocking lines 30 are shown as being linearly straight and oriented parallel with respect to one of pairs opposing edges 21 or 22 of the respective die areas 12. Example blocking lines 30 are shown as being individually of constant width which is the same as width of space between immediately adjacent blocking lines 30, and have constant pitch $P_1$. Alternate configurations such as non-equal and/or non-constant space-width and/or blocking line-width may be used. An example range of multiple wavelengths for the incident radiation is from 250 nm to 850 nm, with an example pitch $P_1$ for blocking lines 30 therefore being less than 250 nm. However in ideal embodiments, pitch $P_1$ of blocking lines 30 is at least 25% less than the smallest wavelength, and in one embodiment at least 50% less than the smallest wavelength. In one embodiment, pitch $P_1$ of blocking lines 30 is less than 150 nm, and in one embodiment less than 100 nm.

Regardless, the blocking lines are designed to reduce spectrum variation to below a detectable level for any (if any) polarized electromagnetic radiation passing to elevationally inward of the blocking lines. In the context of this document, "spectrum variation" is variation in reflectance of any (if any) polarized electromagnetic radiation that passes into and back out of material that is elevationally inward of the blocking lines due to horizontally spaced structures (if any) that are in such material. Ideally, the blocking lines block detectable passage (in one embodiment, all passage) of the polarized electromagnetic radiation elevationally there-through as well as elevationally through the spaces between the blocking lines. Yet in one embodiment, the blocking lines allow some detectable passage of the polarized electromagnetic radiation at least elevationally through the spaces between the blocking lines. The artisan can select suitable shape(s), width(es) and thickness(es) for blocking lines 30 to achieve a desired blocking effect. Such may be determined in part by considering composition of the blocking lines, smallest wavelength of the incident radiation, and blocking line pitch. Ideally, it is expected that blocking line width will be at least 10% of pitch and blocking line thickness will be at least 25% of the smallest wavelength.

In one embodiment and as shown, target 18 has target features 28 that comprise spaced-apart parallel elongated feature lines. In one such embodiment, the feature lines have pitch that is less than the smallest wavelength of the radiation to be used, and in one embodiment blocking lines 30 are oriented perpendicular relative to the feature lines. As alternate embodiments, the blocking lines may be oriented other than perpendicular relative to the feature lines (not shown in FIG. 3), and/or the feature lines may have pitch that is greater than the smallest wavelength of the radiation to be used.

Further, target features 28 are shown as being homogenously filled trenches. Alternately, such trenches may be empty or only partially filled (regardless of homogeneity). Regardless, the line spaces between the depicted trenches may be considered as or may function as target features.

Figure 6:
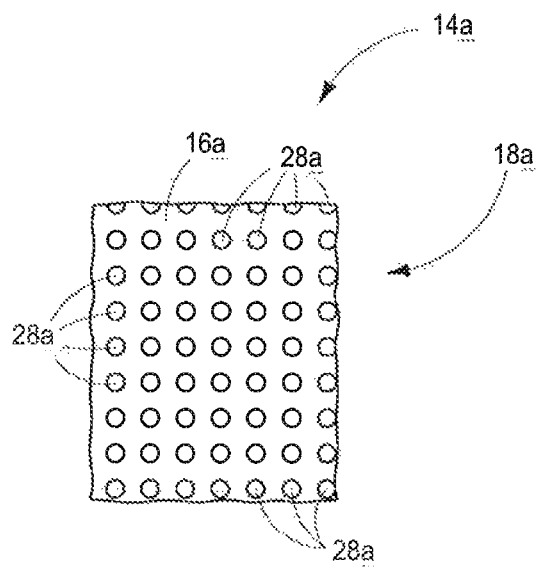
FIG. 6 is a sectional view of an alternate embodiment substrate to that of FIG. 3 that corresponds in position to that taken through line 5-5 in FIG. 3.
Figure 7:
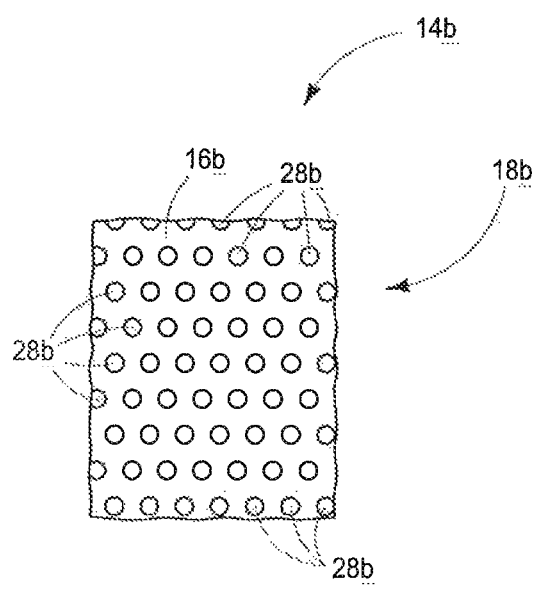
FIG. 7 is a sectional view of another alternate embodiment substrate to that of FIG. 3 that corresponds in position to that taken through line 5-5 in FIG. 3.

Embodiments of the invention also encompass forming a scatterometry target having target features that do not comprise spaced-apart parallel elongated feature lines. By way of examples only, the target features may comprise an array of contact openings or an array of vertically projecting pillars. For example, FIG. 6 shows an alternate embodiment scatterometry target 18a formed relative to an elevationally outermost surface 16a of a substrate 14a. Like numerals from the above-described embodiments have been used where appropriate, with some construction differences being indicated with the suffix "a". FIG. 6 corresponds in position to the cross-section of FIG. 5 and wherein target features 28a individually comprise a contact opening or a vertically projecting pillar within an array of such openings or pillars. FIG. 6 shows an example 2D square lattice for target features 28a. FIG. 7 shows an alternate 2D hexagonal lattice of target features 28b with respect to a scatterometry target 18b relative to outer surface 16b of a substrate 14b. Like numerals from the above-described embodiments have been used where appropriate, with some construction differences being indicated with the suffix "b". Other non-linear 2D layouts may of course be used. Regardless, pitch of the target features may be the same, greater than, or less than the smallest wavelength of the polarized electromagnetic radiation that is to be impinged upon the scatterometry target. Further, target feature pitch may be constant or variable.

It may be desirable to orient the direction of polarization of the polarized electromagnetic radiation to be perpendicular to blocking lines 30 to achieve the desired radiation-blocking effect, particularly where the target features are not lines that are oriented perpendicular relative to the blocking lines and do not have pitch less than the smallest wavelength of the impinging radiation. Regardless, and alternately or additionally, additional spaced-apart parallel elongated blocking lines may be formed at additional elevations above and/or below blocking lines 30, and which respectively may be oriented parallel, perpendicular, or otherwise relative to blocking lines 30.

Figure 8:
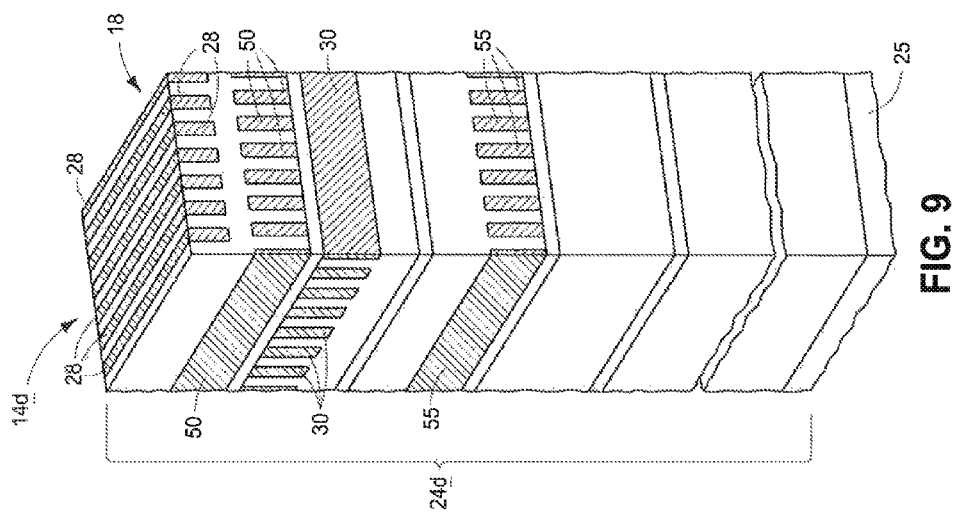
FIG. 8 is a diagrammatic view of still another alternate embodiment substrate to that shown in FIG. 3.

As one example, FIG. 8 shows an alternate substrate 14c corresponding to FIG. 3 yet having a contact opening pattern like that of FIG. 6. Like numerals from the above-described embodiments have been used where appropriate, with some construction differences being indicated with the suffix "c" or with different numerals. While FIG. 8 depicts scatterometry target 18c as being generally of the configuration of FIG. 6, the target design may be of FIG. 3 or of other design. Vertical region 24c of substrate 14c comprises additional spaced-apart parallel elongated blocking lines 50 having an optical property different from that of spaces between additional blocking lines 50. Additional blocking lines 50 are shown as spaced elevationally from and overlapping with target features 28c and blocking lines 30. Additional blocking lines 50 are shown as being elevationally between scatterometry target 18 and blocking lines 30, and are oriented perpendicularly relative to blocking lines 30. Alternate orientations are contemplated. For example, additional blocking lines 50 may be oriented other than perpendicularly relative to blocking lines 30. Further, additional blocking lines 50 may be elevationally below (not shown) blocking lines 30 and if so may be oriented perpendicularly or otherwise relative to blocking lines 30. Additional blocking lines 50 may have pitch that is less than, equal to, or greater than the smallest wavelength of the range of wavelengths of electromagnetic radiation used.

Figure 9:
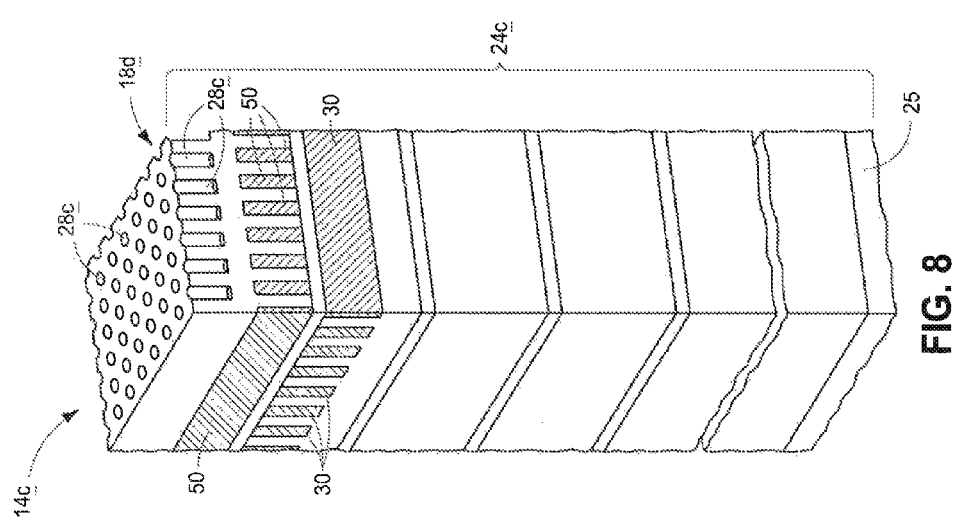
FIG. 9 is a diagrammatic view of yet another alternate embodiment substrate to that shown in FIG. 3.

FIG. 9 illustrates an alternate embodiment substrate 14d usable with methodical aspects of the invention. Like numerals from the above-described embodiments have been used where appropriate, with some construction differences being indicated with the suffix "d" or with different numerals. Vertical region 24d comprises at least one set of additional spaced-apart parallel elongated blocking lines 55 having an optical property different from that of spaces between blocking lines 55. One additional set of lines 55 is shown, although one or more others may be used, for example elevationally inward of lines 55, and regardless of orientation and pitch. Additional blocking lines 55 are within the same vertical region 28d of substrate 14d and are shown spaced elevationally from and overlapping with target features 28d, blocking lines 30, and blocking lines 50.

Embodiments of the invention include forming a scatterometry target relative to an elevationally outermost surface of a substrate. The scatterometry target comprises features having an optical property that is different from that of spaces between the features. The substrate comprises spaced-apart parallel elongated blocking lines having an optical property different from that of spaces between the blocking lines. The blocking lines are elevationally inward of the target features. The target features and the blocking lines overlap within a same vertical region of the substrate. Polarized electromagnetic radiation having multiple wavelengths is impinged onto the scatterometry target. Pitch of the blocking lines is less than the smallest wavelength of the impinged radiation. The blocking lines reduce spectrum variation to below a detectable level for any (if any) polarized electromagnetic radiation passing to elevationally inward of the blocking lines. Electromagnetic radiation that is reflected from the scatterometry target from the impinging is detected, and therefrom a property associated with the target features and/or spaces between the target features is determined. Structures and systems as described above may be used.

In one embodiment, the determining is of the dimension of the target features and/or spaces between the target features. In one embodiment, the determining is of shape of the target features and/or spaces between the target features. In one embodiment, the determining is of a thickness of the target features and/or thickness of material of the spaces between the target features. Regardless of what is determined or whether more than one thing is determined, the method may be essentially repeated with another scatterometry target at the same or another elevationally outermost surface with respect to another set of blocking lines which overlap with features of the another target in another vertical region of the substrate. Such another vertical region of the substrate may have any of the other attributes described above.

Embodiments of the invention may result in certain advantages over prior scatterometry metrology methods. For example as described in the Background section, radiation impinged upon a scatterometry target partially reflects from and partially passes through the target. The passing radiation typically continues through all of the various material and structure to the base substrate before it is reflected back out of the substrate to be detected by the detector and ultimately analyzed. Therefore in modeling to create the theoretical spectra for comparison with that which is actually received, the modeling software must take into account the material and structure of everything beneath the scatterometry target as well as material and structure of the scatterometry target itself. With some scatterometry metrology methods in accordance with the invention using blocking lines that block detectable passage of electromagnetic radiation, the modeling can neglect what becomes a non-existent effect of reflected radiation that would have passed through the material that is between the blocking lines and the base substrate but does not due to the impinging radiation being blocked by the blocking lines. Regardless, blocking lines are used that at least reduce spectrum variation to below a detectable level for any polarized electromagnetic radiation passing to elevationally inward of the blocking lines. Accordingly, the modeling of the theoretical spectra might be simplified and might ultimately be more accurate, for example by not having to consider variation (if any) of the deposition, processing, patterning, and spectral analysis associated with the material and structure beneath the blocking lines.

Additionally or alternately, placing one or more blocking line gratings at different levels within street area of a substrate comprising spaced die areas may reduce dishing of those street areas during polishing. Thereby, the street area target features can be very close to or at the same elevation of operable features that are patterned within the die areas.

Embodiments of the invention also encompass a method of modeling formation of a vertical region of a multilayer semiconductor substrate so that it will comprise a scatterometry target. Such a method includes selecting a scatterometry target design for formation of a scatterometry target relative to an elevationally outermost surface of a vertical region of a semiconductor substrate. The scatterometry target design comprises spaced-apart features that will have an optical property on the substrate that is different from that of spaces on the substrate between the features. The method of modeling includes designing a blocking grating that will be formed within the vertical region on the substrate prior to forming the scatterometry target of the scatterometry target design. The blocking grating will be formed elevationally inward of and overlap with the scatterometry target. The designing comprises determining pitch of blocking lines of the blocking grating that will be less than a smallest wavelength of polarized electromagnetic radiation having multiple wavelengths that is to be impinged upon the scatterometry target. The designing comprises determining an orientation of the blocking lines so that the blocking lines of the blocking grating will reduce spectrum variation to below a detectable level for any polarized electromagnetic radiation passing to elevationally inward of the blocking lines. Accordingly, certain embodiments of the invention comprise modeling without necessarily carrying out actual scatterometry metrology on a physical substrate, for example using modeling software as described above. Such modeling however, for example, may use any of the aspects described above and with respect to FIGS. 1-9.

CONCLUSION

In some embodiments, a scatterometry metrology method comprises forming a scatterometry target relative to an elevationally outermost surface of a substrate. The scatterometry target comprises features having an optical property that is different from that of spaces between the features. The substrate comprises spaced-apart parallel elongated blocking lines having an optical property different from that of spaces between the blocking lines. The blocking lines are elevationally inward of the target features. The target features and the blocking lines overlap within a same vertical region of the substrate. Polarized electromagnetic radiation having multiple wavelengths is impinged onto the scatterometry target. Pitch of the blocking lines is less than the smallest wavelength of the impinged radiation. The blocking lines reduce spectrum variation to below a detectable level for any polarized electromagnetic radiation passing to elevationally inward of the blocking lines. Electromagnetic radiation that is reflected from the scatterometry target from the impinging is detected, and therefrom a property associated with the target features and/or spaces between the target features is determined.

In some embodiments, a method comprises modeling formation of a vertical region of a multilayer semiconductor substrate so that it will comprise a scatterometry target. Such a method comprises selecting a scatterometry target design for formation of a scatterometry target relative to an elevationally outermost surface of a vertical region of a semiconductor substrate. The scatterometry target design comprises spaced-apart features that will have an optical property on the substrate that is different from that of spaces on the substrate between the features. The method of modeling includes designing a blocking grating that will be formed within the vertical region on the substrate prior to forming the scatterometry target of the scatterometry target design. The blocking grating will be formed elevationally inward of and overlap with the scatterometry target. The designing comprises determining pitch of blocking lines of the blocking grating that will be less than a smallest wavelength of polarized electromagnetic radiation having multiple wavelengths that is to be impinged upon the scatterometry target. The designing comprises determining an orientation of the blocking lines so that the blocking lines of the blocking grating will reduce spectrum variation to below a detectable level for any polarized electromagnetic radiation passing to elevationally inward of the blocking lines.

In compliance with the statute, the subject matter disclosed herein has been described in language more or less specific as to structural and methodical features. It is to be understood, however, that the claims are not limited to the specific features shown and described, since the means herein disclosed comprise example embodiments. The claims are thus to be afforded full scope as literally worded, and to be appropriately interpreted in accordance with the doctrine of equivalents.

The invention claimed is:

1. A scatterometry metrology method, comprising:
    forming a scatterometry target relative to an elevationally outermost surface of a substrate, the scatterometry target comprising features having an optical property different from that of spaces between the features, the substrate comprising spaced-apart parallel elongated blocking lines having an optical property different from that of spaces between the blocking lines, the blocking lines being elevationally inward of the target features, the target features and the blocking lines overlapping within a same vertical region of the substrate;
    impinging polarized electromagnetic radiation having multiple wavelengths onto the scatterometry target, pitch of the blocking lines being less than the smallest wavelength of the impinged radiation, the blocking lines reducing spectrum variation to below a detectable level for any polarized electromagnetic radiation passing to elevationally inward of the blocking lines; and
    detecting electromagnetic radiation that is reflected from the scatterometry target from the impinging and determining therefrom a property associated with the target features and/or spaces between the target features.

2. The method of claim 1 wherein the blocking lines allow some detectable passage of the polarized electromagnetic radiation at least elevationally through the spaces between the blocking lines.

3. The method of claim 1 wherein the blocking lines block detectable passage of the polarized electromagnetic radiation elevationally there-through as well as elevationally through the spaces between the blocking lines.

4. The method of claim 3 wherein the blocking lines block all passage of the polarized electromagnetic radiation elevationally there-through as well as elevationally through the spaces between the blocking lines.

5. The method of claim 3 wherein the substrate comprises a base substrate and material elevationally between the base substrate and the blocking lines, the determining comprising neglecting non-existent effect of radiation from the base substrate that would have passed back through the material but does not due to the impinging radiation being blocked by the blocking lines.

6. The method of claim 1 wherein the blocking lines comprise metal.

7. The method of claim 1 wherein the blocking lines are elevationally spaced from the target features.

8. The method of claim 1 wherein the target features comprise spaced-apart parallel elongated feature lines.

9. The method of claim 8 wherein the feature lines have pitch that is less than said smallest wavelength.

10. The method of claim 8 wherein the blocking lines are oriented perpendicular relative to the feature lines.

11. The method of claim 10 wherein the feature lines have pitch that is less than said smallest wavelength.

12. The method of claim 1 wherein the target features do not comprise spaced-apart parallel elongated feature lines.

13. The method of claim 12 wherein the target features comprise an array of contact openings or an array of vertically projecting pillars.

14. The method of claim 1 wherein direction of polarization of the polarized electromagnetic radiation is perpendicular to the blocking lines.

15. The method of claim 14 wherein the target features comprise spaced-apart parallel elongated feature lines.

16. The method of claim 14 wherein the target features do not comprise spaced-apart parallel elongated feature lines.

17. The method of claim 14 wherein the target features have pitch that is greater than said smallest wavelength.

18. The method of claim 1 wherein the substrate comprises additional spaced-apart parallel elongated blocking lines having an optical property different from that of spaces between the additional blocking lines, the additional blocking lines being within the same vertical region and being spaced elevationally from and overlapping with the target features and the first-stated blocking lines.

19. The method of claim 18 wherein the additional blocking lines are elevationally between the target and the first-stated blocking lines and are oriented perpendicular to the first-stated blocking lines.

20. The method of claim 19 wherein the additional blocking lines have pitch that is less than said smallest wavelength.

21. The method of claim 20 wherein the target features have pitch that is greater than said smallest wavelength.

22. The method of claim 18 wherein the additional blocking lines are elevationally below the first-stated blocking lines and are oriented perpendicular to the first-stated blocking lines.

23. The method of claim 18 wherein the substrate comprises at least one set of additional spaced-apart parallel elongated blocking lines having an optical property different from that of spaces between the blocking lines in the respective set, the at least one set of additional blocking lines being within the same vertical region and being spaced elevationally from and overlapping with the target features, the first-stated blocking lines, and the first-stated additional blocking lines.

24. The method of claim 1 comprising repeating the method with another of said scatterometry target at another elevationally outermost surface and another of said blocking lines overlapping in another of said same vertical region of the substrate.

25. The method of claim 1 wherein the pitch of the blocking lines is at least 25% less than said smallest wavelength.

26. The method of claim 1 wherein the pitch of the blocking lines is at least 50% less than said smallest wavelength.

27. The method of claim 1 wherein the pitch of the blocking lines is less than 150 nanometers.

28. The method of claim 1 wherein the pitch of the blocking lines is less than 100 nanometers.

29. The method of claim 1 wherein width of the blocking lines is at least 10% of pitch and thickness of the blocking lines is at least 25% of said smallest wavelength.

30. The method of claim 1 wherein the determining is of a dimension of the target features and/or spaces between the target features.

31. The method of claim 1 wherein the determining is of shape of the target features and/or spaces between the target features.

32. The method of claim 1 wherein the determining is of thickness of the target features and/or thickness of material of the spaces between the target features.

33. The method of claim 1 wherein the substrate comprises a plurality of rectangular die areas and street area therebetween, the scatterometry target being formed in the street area, the blocking lines being linearly straight and oriented parallel with respect to one of a pair of opposing edges of the respective die areas.

34. A method of modeling formation of a vertical region of a multilayer semiconductor substrate to comprise a scatterometry target, comprising:
    selecting a scatterometry target design for formation of a scatterometry target relative to an elevationally outermost surface of a vertical region of a semiconductor substrate, the scatterometry target design comprising spaced-apart features that will have an optical property on the substrate that is different from that of spaces on the substrate between the features; and
    designing a blocking grating that will be formed within the vertical region on the substrate prior to forming the scatterometry target of the scatterometry target design, the blocking grating to be formed elevationally inward of and overlapping with the scatterometry target, the designing comprising determining pitch of blocking lines of the blocking grating that will be less than a smallest wavelength of polarized electromagnetic radiation having multiple wavelengths to be impinged upon the scatterometry target, the designing comprising determining an orientation of the blocking lines so that the blocking lines of the blocking grating will reduce spectrum variation to below a detectable level for any polarized electromagnetic radiation passing to elevationally inward of the blocking lines.

35. The method of claim 34 wherein the blocking grating comprises metal-comprising lines.

\* \* \* \* \*